(12) United States Patent
Betbeder et al.

(10) Patent No.: US 9,731,005 B2
(45) Date of Patent: Aug. 15, 2017

(54) PHARMACEUTICAL COMPOSITION COMPRISING A SOLID NANOPARTICLE AND AT LEAST AN ANTIGEN FOR THE TREATMENT AGAINST AN INTRACELLULAR PATHOGENIC AGENT

(71) Applicants: UNIVERSITÉ DE DROIT ET DE SANTÉ DE LILLE II, Lille (FR); UNIVERSITÉ DE TOURS FRANCOIS RABELAIS, Tours (FR); CENTRE HOSPITALIER RÉGIONAL UNIVERSITAIRE DE LILLE, Lille (FR)

(72) Inventors: Didier Betbeder, Houplin Ancoisne (FR); Isabelle Dimier-Poisson, Tours (FR); Céline Ducournau, Louans (FR)

(73) Assignees: UNIVERSITE DE DROIT ET DE SANTE DE LILLE II (FR); UNIVERSITE DE TOURS FRANCOIS RABELAIS (FR); CENTRE HOSPITALIER REGIONAL UNIVERSITAIRE DE LILLE (FR)

( * ) Notice: Subject to any disclaimer, the term of this patent is extended or adjusted under 35 U.S.C. 154(b) by 68 days.

(21) Appl. No.: 14/428,588

(22) PCT Filed: Sep. 13, 2013

(86) PCT No.: PCT/IB2013/002372
§ 371 (c)(1),
(2) Date: Mar. 16, 2015

(87) PCT Pub. No.: WO2014/041427
PCT Pub. Date: Mar. 20, 2014

(65) Prior Publication Data
US 2015/0238598 A1    Aug. 27, 2015

(30) Foreign Application Priority Data
Sep. 17, 2012 (EP) .................................. 12370002

(51) Int. Cl.
| A61K 39/00 | (2006.01) |
| A61K 39/02 | (2006.01) |
| A61K 39/04 | (2006.01) |
| A61K 39/39 | (2006.01) |
| A61K 9/00 | (2006.01) |
| A61K 9/51 | (2006.01) |
| A61K 39/002 | (2006.01) |
| A61K 47/48 | (2006.01) |

(52) U.S. Cl.
CPC ............ *A61K 39/39* (2013.01); *A61K 9/0043* (2013.01); *A61K 9/5123* (2013.01); *A61K 9/5161* (2013.01); *A61K 39/00* (2013.01); *A61K 39/002* (2013.01); *A61K 47/48923* (2013.01); *A61K 2039/543* (2013.01); *A61K 2039/55555* (2013.01); *A61K 2039/57* (2013.01); *A61K 2039/6018* (2013.01); *A61K 2039/6087* (2013.01)

(58) Field of Classification Search
CPC .......... A61K 39/00; A61K 39/02; A61K 39/04
USPC ....................... 424/234.1; 977/700, 702, 773
See application file for complete search history.

(56) References Cited

PUBLICATIONS

Debin, A., et al. Vaccine, vol. 20, pp. 2752-2763, 2002.*
Stanley, A.C., et al. Vaccine vol. 22, No. 29-30, pp. 3929-3941, 2004.*
International Search Report dated Feb. 7, 2014 issued in corresponding International patent application No. PCT/IB2013/002372.
Arnaud Debin et al.: "Intranasal immunization with recombinant antigens associated with new cationic particles induces strong mucosal as well as systemic antibody and CTL responses", Vaccine, Elsevier Ltd, GB, vol. 20, No. 21-22, Jun. 21, 2002, pp. 2752-2763, XP002657642.
Yolken R H et al., "Antibodies to Toxoplasma gondii in individuals with first-episode schizophrenia." Clinical Infectious Diseases: An Official Publication of the Infectious Diseases Society of America, vol. 32, No. 5, Mar. 1, 2001, pp. 842-844, XP002699831.
Christophe Youta Dombu et al., "Characterization of endocytosis and exocytosis of cationic nanoparticles in airway epithelium celss; Characterization of endocytosis and exocytosis of cationic nanoparticles in airway epithelium cells", Nanotechnology, 10P, Bristol, GB, vol. 21, No. 35, Aug. 6, 2010, p. 355102, XP020197388.
Baudner B C et al.: "Enhancement of protective efficacy following intranasal immunization with vaccine plus a nontoxic LTK63 mutant delivered with nanoparticles.", Infection and Immunity vol. 70, No. 9, Sep. 2002, pp. 4785-4790, XP002699832.
Archibald Paillard et al.: "Positively-Charged Porous Polysaccharide Nanoparticles Loaded with Anionic Molecules Behave as 'Stealth' Cationic Nanocarriers", Pharmaceutical Research, vol. 27, No. 1, Jan. 1, 2010, pp. 126-133, XP055005503.
Merhi Maysaloun et al., "Study of serum interaction with a cationic nanoparticle: implications for in vitro endocytosis, cytotoxicity and genotoxicity.", International Journal of Pharmaceutics Feb. 14, 2012, vol. 423, No. 1, XP002699833.
Prieur et al.: "Combination of human cytomegalovirus recombinant immediate-early protein (IE1) with 80 nm cationic bivectors: protection from proteolysis and potentiation of presentation to CD4<+> T-cell clones in vitro", Vaccine, Elsevier Ltd, GB, vol. 14, No. 6, Apr. 1, 1986, pp. 511-520, XP004057280.

(Continued)

*Primary Examiner* — Rodney P Swartz
(74) *Attorney, Agent, or Firm* — Ostrolenk Faber LLP (57) ABSTRACT

A pharmaceutical composition for its use in the prophylactic treatment of a patient against an intracellular pathogen, said composition comprising a solid nanoparticle comprising a porous cationic-polysaccharide solid core, loaded with at least an anionic phospholipid, without said cationic-polysaccharide core being surrounded by any phospholipidic layer, and at least an antigen obtained from said pathogen.

20 Claims, 4 Drawing Sheets

(56) References Cited

PUBLICATIONS

Razafindratsita et al: "Improvement of sublingual immunotheraphy efficacy with a mucoadhesive allergen formulation", Journal of Allergy and Clinical Immunology, Elsevier, Amsterdam, NL, vol. 120, No. 2, Jul. 29, 2007, pp. 278-285, XP02219978.

Database Medline [online] US National Library of Medicine (NLM), Bethesda, MD, US; Jun. 2009, Wu Liang et al.: "[In vitro culture of Toxoplasma gondii tachzoites in HFF and HeLa cells]", XP002699834, database accession No. NLM19852365 abstract.

Sibley L D et al: "Toxoplasma gondii: secretion of a potent nucleoside triphosphate hydrolase into the parasitophorous vacuole." Experimental Parasitology, vol. 79, No. 3, Nov. 1994, pp. 301-311, XP002699835.

Axxoux Samiro et al.: "Toxoplasma gondii: identification and immune response against a group of proteins involved in cellular invasion", Experimental Parasitology, vol. 130, No. 1, Jan. 2012, pp. 63-68, XP002699836.

Dimier-Poisson, Isabelle, et al. "Porous nanoparticles as delivery system of complex antigens for an effective vaccine against acute and chronic Toxoplasma gondii infection." Biomaterials 50 (2015): 164-175.

Siegrist, Claire-Anne. "Vaccine immunology." Vaccines 5 (2008): 1725.

Major, M., et al. "Characterisation and phase behaviour of phospholipid bilayers adsorbed on spherical polysaccharidic nanoparticles." Biochimica et Biophysica Ada (BBA)-Biomembranes 1327.1 (1997): 32-40.

* cited by examiner

PHARMACEUTICAL COMPOSITION COMPRISING A SOLID NANOPARTICLE AND AT LEAST AN ANTIGEN FOR THE TREATMENT AGAINST AN INTRACELLULAR PATHOGENIC AGENT

CROSS REFERENCE TO RELATED APPLICATIONS

The present application is a 35 U.S.C. §371 National Phase conversion of PCT/IB2013/002372, filed Sep. 13, 2013, which claims benefit of European Application No. 12370002.3, filed Sep. 17, 2012, the disclosure of which is incorporated herein by reference. The PCT International Application was published in the English language.

TECHNICAL FIELD

The present invention relates to a pharmaceutical composition that may be used in the preventive treatment of infections caused by an intracellular pathogen like, for instance, a virus, a bacterium or a parasite and more particularly *Toxoplasma gondii*.

PRIOR ART

*Toxoplasma gondii* (hereinafter *T. gondii*) is a species of parasite protozoa in the genus *Toxoplasma*. The definitive host of *T. gondii* is the felids, but the parasite can be carried by many warm-blooded animals (birds, cattle, sheep and also humans). The life cycle of *T. gondii* has two phases. The sexual part of the life cycle (coccidia like) takes place only in cats, both domestic and wild, which makes cats the parasite's primary host. The second phase, the asexual part of the life cycle, can take place in another warm-blooded animal called intermediate host.

*T. gondii* exists in three forms:
  The tachyzoite is always intracellular and replicates in intermediate host's cells, the tachyzoite form is not readily able to invade all cells of the intermediate host ("contaminant" or disseminated) and can be easily destroyed when it is outside the cell;
  The bradyzoite contained in cysts, mainly in the tissues of the intermediate host's muscles and brain, where the immune response is low; this form is contaminant (contagious per os);
  The sporozoite contained in sporulated oocyst which is the form able to survive out of the intermediate and primary host; this form is also contaminant per os.

Toxoplasmosis, the disease of which *T. gondii* is the causative agent, is usually minor and self-limiting but can have serious or even fatal effects on a fetus whose mother first contracts the disease during pregnancy or on an immune-deficient patient. In cattle and sheep, for example, toxoplasmosis is a main cause of abortion and thus generates great losses.

Recently it has been postulated that *Toxoplasma* has some degree of causal relation to schizophrenia. This postulate rests on the positive relationships between the prevalence of *Toxoplasma* antibodies and the development of schizophrenia. Yolken et al. provides one example of the value of integrating behavioral effects of *Toxoplasma* in models of emotional and psychiatric conditions (Yolken R H, Bachmann S, Rouslanova I, Lillehoj E, Ford G, Fuller Torrey E et al. Antibodies to *Toxoplasma gondii* in individuals with first-episode schizophrenia. Clin. Infect. Dis. 2001; 32: 842-44.).

Accordingly, one purpose of the present invention is to provide a pharmaceutical composition enabling a vaccine for a patient against an intracellular pathogen, more particularly against an intracellular parasite like, for instance, a protozoa and more particularly, *T. gondii*.

BRIEF SUMMARY OF THE INVENTION

The present invention relates to a pharmaceutical composition comprising, as an active ingredient, the mixture of:
  a solid nanoparticle comprising a porous cationic-polysaccharide core, loaded with at least an anionic phospholipid and without any phospholipidic layer surrounding said core;
  at least an antigen obtained from said pathogenic agent; and
  a pharmaceutically acceptable solvent.

More particularly, the invention relates to the aforementioned pharmaceutical composition for its use in the prophylactic treatment against an intracellular pathogenic agent in a patient or in the prophylactic treatment of a disease or infection caused by an intracellular pathogenic agent.

According to the invention, the term "treatment" refers to any indicia of success in the treatment or amelioration or prevention of the disease, condition, or disorder, including any objective or subjective parameter such as abatement, remission, diminishing of symptoms or making the disease condition more tolerable to the patient, slowing in the rate of degeneration or decline, or making the final point of degeneration less debilitating. The treatment or amelioration of symptoms can be based on objective or subjective parameters, including the results of an examination by a physician.

The term "treatment" also refers to any decrease of the amount of the pathogenic agent in the patient's body or to any alteration of the pathogenic agent, even over a short time period. When the pathogenic agent has several forms including extracellular forms, a decrease or a modification of at least one pathogenic agent's form is considered as a treatment effect. If the pathogenic agent may be present in several organs of the patient's body, a decrease of the amount of pathogenic agent or a modification of the pathogenic agent in at least one organ is considered as a treatment effect.

Accordingly, the term "treating" includes the administration of the composition of the invention to prevent or delay, to alleviate, or to arrest or inhibit development of the symptoms or conditions associated with a disease, condition or disorder as described herein. The term "therapeutic" refers at least to the partial reduction, elimination, or prevention of the disease, symptoms of the disease, or side effects of the disease in the subject.

The term "prophylactic" means that the treatment is able to prevent or delay the onset of the disease, or is able to prevent the manifestation of clinical or subclinical symptoms thereof.

The terms "pharmaceutically acceptable" refer to those solvent, compounds, materials, compositions, or dosage forms which are, within the scope of sound medical judgment, suitable for contact with the tissues of human beings and animals without excessive toxicity, irritation, allergic response, or other problematic complications commensurate with a reasonable benefit/risk ratio.

According to one aspect of the invention, the invention relates to the before-mentioned composition for use as a medicament and particularly as an immunogenic medicament enabling a cellular immune response in a patient.

However, the present invention is not limited to a Th1 immune response (cellular response). The pharmaceutical composition may also induce the production of specific antibodies (humoral response) or induce both responses. In the present invention, "immune response" means any reaction by the immune system, a cellular immune response and/or an humoral immune response. These reactions include the alteration in the activity of an organism's immune system in response to an antigen and can involve, for example, antibody production, induction of cell-mediated immunity, complement activation, or development of immunological tolerance. The immune response may be a Th1 response or a Th2 response or a mixture thereof. The term "immunogenic" refers to the capacity of inducing an immune response, directly or not.

According to the present invention, the nanoparticle core is charged with at least a phospholipid. Accordingly, the solid core is porous and the pores thereof are filled with a phospholipid or a mixture of at least two lipids or phospholipids. The nanoparticle core is made of a cationic polysaccharide or a mixture of at least two cationic-polysaccharides. It may also be made of any other compound that is co-polymerized or not co-polymerized with said cationic polysaccharide(s).

According to the invention, the nanoparticle core is not surrounded by any phospholipidic layer. A phospholipidic layer is defined as a layer comprising at least one phospholipid.

The cationic polysaccharide may be a crosslinked polymer and may be obtained by the reaction between a polysaccharide chosen from among starch, dextran, dextrin, and maltodextrin, derivatized with cationic ligands such as quaternary ammonium salts. Primary, secondary and tertiary amines may also be used. More particularly, the cationic polysaccharide can be obtained from the reaction between maltodextrin and glycidyl-trimethylammonium.

The anionic phospholipid may be chosen from among glycerol phospholipids and may be, for instance, diacylphosphatidyl glycerol such as diacylphosphatidyl serine, diacylphosphatidyl inositol and dipalmitoylphosphatidylglycerol (DG).

The following experimental results show that at least in the case of *T. gondii*, the composition of the invention induces the production of specific IFN-γ against *T. gondii*. In the case of toxoplamosis, it is known that host resistance seems to occur via synthesis of IFN-γ by NK cells and adaptive T lymphocytes. Following infection, antigen-presenting cells synthesize TNF-α and IL-12 which induce NK cells to secrete IFN-γ. The combined action of IL-12 and IFN-γ induce a strong differentiation of T helper precursors into Th1 lymphocytes. These CD4+ T cells then synthesize large amounts of IFN-γ and IL-2. These two cytokines finally induce CD8+T lymphocytes proliferation and IFN-γ secretion. Thus protection against *T. gondii* infection is mainly attributed to cell-mediated immunity. Therefore, the composition of the invention can also protect the fetus when the mother has been treated with the composition/vaccine of the invention.

According to the invention, the intracellular pathogenic agent is an intracellular pathogen that may be a virus, a bacteria, a mycobacteria, a fungus or a parasite. An intracellular pathogenic agent is defined as any micro or macro organism having at least one intracellular form. The term "pathogenic" refers to an agent able to involve physiological and/or psychological changes in the patient or in the patient's progeny or offsprings.

Herpes simplex virus 1 and 2, human papillomavirus, Epstein-Barr virus, cytomegalovirus, *Mycobacterium tuberculosis*, dengue fever virus, HIV, Human respiratory syncytial virus (RSV), hepatitis A, virus, hepatitis B virus and hepatitis C virus may be cited as examples of intracellular pathogenic agents.

A "parasite" means, according to the invention, any micro or macro organism which benefits at the expense of another called "the host". According to the invention, the term parasite includes macroparasites (typically helminths) and microparasites (typically protozoa) and all of the forms that may take during their life cycle.

When the pathogenic agent is a parasite having an intracellular form during its life-cycle, it may be chosen from among apicomplexan intracellular parasites, like, for instance *Toxoplasma gondii*, *Emeria* spp, *Neospora caninum*, *Sarcocystis* spp, *Plasmodium* spp (*Plasmodium falciparum, Plasmodium vivax, Plasmodium ovale, Plasmodium malariae, Plasmodium knowlesi* for instance and *Cryptosporidium* spp. It may also be chosen from among *Acanthamoeba* spp., *Babesia* spp., *Balantidium coli, Blastocystis, Dientamoeba fragilis, Entamoeba histolytica, Giardia lamblia, Isospora belli, Leishmania* spp., *Naegleria fowleri, Rhinosporidium seeberi, Trichomonas vaginalis, Trypanosoma brucei*, and *Trypanosoma cruzi*. These parasites are known as at least human and veterinary parasites.

According to the present invention, the terms "antigen obtained from the pathogenic agent" may be any antigen or mixture thereof known and already used to obtain an immune response in a patient against said pathogenic agent. These terms refer to native antigen(s) or mixtures thereof as well as recombinant antigen(s) or mixtures thereof and mixture(s) of native and recombinant antigens. The antigen may be a protein, particularly a surface protein. The term "antigen" refers to any substance able to induce by itself (directly) an immune response and/or to any substance able to induce an immune response by combining with some products of an immune response once they are made.

According to the invention, the antigen may be derived from any form of the pathogenic agent. The pathogenic agent itself may be used alive, killed or attenuated for providing said antigen or mixture thereof.

The antigen or antigen mixture may be obtained from infected cells. The intracellular pathogen contained in these infected cells is then extracted, for example by destroying the cell membrane. Depending on the technique used for lysing cell membrane, the pathogenic agent may be killed in the same time.

According to an aspect of the invention, the antigen is obtained from a previously killed pathogenic agent. When the pathogenic agent is a parasite and particularly a protozoa that can be a tachyzoite, the antigen may be obtained from said tachyzoite and particularly from a previously killed tachyzoite.

The inventors have found that the tachyzoite form of *T. gondii*, which is intracellular but not contaminant (disseminated), provides at least one efficient antigen for the prophylaxis of toxoplasmosis. The antigen(s) may be present in a mixture obtained from infected cells containing tachyzoites.

The term "patient" refers to a warm-blooded animal such as a mammal which is afflicted with, or has the potential to be afflicted with one or more diseases and conditions described herein. The term "patient" as used herein includes both humans and non-humans and includes but is not limited to humans, non-human primates, ovines (sheep, goat . . . ), canines, felines, murines, bovines, equines, and porcines. The patient may also be a bird.

The present invention also relates to a vaccine against an intracellular pathogen comprising the pharmaceutical composition of the invention and further comprising a suitable excipient and/or a suitable carrier and/or a suitable vehicle.

Carriers, excipients, diluents and/or adjuvants are chosen according to the route of administration. They may be chosen from among lactose, dextrose sucrose, sorbitol, mannitol, starches, gum acacia, calcium phosphate, alginates, gelatin, calcium silicate, microcrystalline cellulose gelatin, calcium silicate, microcrystalline cellulose, polyvinylpyrrolidone, polyethylene glycol, cellulose, (sterile) water, methylcellulose, methyl and propylhydroxybenzoates, talc, magnesium stearate, edible oils, vegetable oils and mineral oils or suitable mixtures thereof. The pharmaceutical compositions can optionally contain other substances that are commonly used in pharmaceutical formulations, such as lubricating agents, wetting agents, emulsifying and suspending agents, dispersing agents, disintegrating agents, stabilizing agents, isotonic agents, bulking agents, fillers, preserving agents, sweetening agents, flavoring agents, perfuming agents, coloring agents, antibacterial agents and/or antifungal agents such as parabens, chlorobutanol, phenol, sorbic acid, dispensing agents, flow regulators, release agents, etc.

The term "vaccine" relates to a product able to prevent infection caused by an intracellular pathogenic agent upon future exposure thereto.

The composition and/or the vaccine of the invention can be variously administered. For example, the composition/vaccine may be formulated to be orally or topically or enterally or non-parenterally administered. The terms "oral", "enteral", "enterally", "orally", "non-parenteral", "non-parenterally", and the like, refer to administration of a composition to an individual by a route or mode along the alimentary canal. Examples of "oral" routes of administration of a composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g. using suppositories.

The term "topically administrated" refers to the application of a pharmaceutical agent to the external surface of the skin or the mucous membranes (including the surface membranes of the nose, lungs and mouth), such that the agent crosses the external surface of the skin or mucous membrane and enters the underlying tissues. Topical administration can result in a limited distribution of the agent to the skin and surrounding tissues or, when the agent is removed from the treatment area by the bloodstream, systemic distribution of the agent.

The composition and/or the vaccine according to the present invention may be formulated for intranasal administration. The term "intranasal administration" refers to any form of administration whereby an active ingredient is propelled or otherwise introduced into the nasal passages of a subject so that it contacts the respiratory epithelium of the nasal cavity, from which it is absorbed into the systemic circulation. Nasal administration can also involve contacting the olfactory epithelium, which is located at the top of the nasal cavity between the central nasal septum and the lateral wall of each main nasal passage.

The present invention also relates to the use of a nanoparticle comprising a cationic-polysaccharide solid core which is porous, loaded with an anionic phospholipid without being surrounded by any phospholipidic layer, as a vaccine adjuvant. As explained hereinafter, the nanoparticles used in the composition of the invention can be used as a vaccine adjuvant and are at least as efficient as cholera toxin.

The polysaccharide and/or the phospholipid(s) may be chosen as described above as regards to the pharmaceutical composition of the invention.

The present invention also relates to a method for eliciting an immune response against an intracellular pathogen in a patient, said method comprising administrating to a patient a therapeutic amount of a composition of the invention or a vaccine of the invention.

According to one aspect of the method of the invention, the immune response comprises a Th1 response.

The present invention also relates to the use of a pharmaceutical composition as previously described for the fabrication of a vaccine against an intracellular pathogenic agent.

According to the present invention, the amount of antigen(s) contained in the vaccine of the invention is not limited to a determined value. For instance, the composition may comprise from 5 µg to 1 mg of antigen(s), more particularly from 10 µg to 1 mg of antigen(s) and for example from 15 µg to 200 µg of antigen(s).

The present invention also relates to a kit comprising a vaccine of the invention and a leaflet.

DESCRIPTION OF THE EMBODIMENTS

Experimental Part

Preparation of Nanoparticles

Polysaccharide particles are prepared from US Pharmacopoeia maltodextrin, as described previously (Paillard, A., et al, "Positively-charged, porous, polysaccharide nanoparticles loaded with anionic molecules behave as 'stealth' cationic nanocarriers" Pharm. Res. 27:126-33, 2010). Briefly, 100 g of maltodextrin were dissolved in 2N sodium hydroxide with magnetic stirring at room temperature. Further, 1-chloro-2,3-epoxy propane (epichlorhydrin) and glycidyl-trimethylammonium chloride (hydroxycholine, cationic ligand) is added to make cationic polysaccharide gel. The gel is then neutralized with acetic acid and sheared under high pressure in a Minilab homogenisor (Rannie; APV Baker, Evreux, France). The 60 nm polysaccharide nanoparticles obtained are ultra-filtered on an SGI Hi-flow system (hollow fiber module: 30 UFIB/1 S.6/40 kDa; Setric Génie Industriel, France) to remove low molecular weight reagents and salts. The obtained nanoparticles are hereinafter called NPS.

Some of the previous NPS are loaded with anionic phospholipids. Anionic phospholipids are loaded into these porous NPS by injecting an ethanol solution of dipalmitoylphosphatidyl glycerol (DPPG). The porous nanoparticles containing a phospholipid are hereinafter called DGNP. The core of these nanoparticles is not surrounded by any phospholipid layer.

Synthesis and Purification of Total Antigen Extract (TE) of T. gondii

Tachyzoites are obtained from successive splitting of infected HFF cells (Human Foreskin Fibroblasts). About $1 \times 10^8$ tachyzoites derive from one 225 cm² culture flask corresponding to 200 μg of TE. Lysis of tachyzoites is then performed by freeze/thaw cycles, pooled, sonicated (2×10 min, 60 W in ice) and protein amount is evaluated by micro BCA method.

TE refers to the product obtained from tachyzoites according to the process as above described. TE is used for mice immunization in combination with nanoparticles (NPS and DGNP), Elisa coating and cellular restimulation test. TE is a mixture of several antigens.

Vaccination and Challenge Protocol-Choice Between NP and DGNP

The most effective nanoparticles as antigen carriers were determined on the basis of intensity of humoral and cellular responses and protection.

Adult females Swiss and CBA/J mice of 20-25 g and 6-8 weeks were purchased from Janvier (France). The animal experiments comply with the French Government's ethical and animal experiment regulations.

Swiss mice received an intranasal treatment, three times at 15-day intervals, with TE (10 μg) and DGNP nanoparticles (30 μg) alone (defined as control groups) or with the combination TE+NPS, TE+DGNP (10 μg of TE and 30 μg of NPS or DGNP).

Each dose of the above-mentioned total extract (TE), nanoparticles and mixtures thereof was diluted to a final volume of 10 μl in phosphate-buffered saline (10 mM phosphate, 140 mM NaCl [PBS]) and instilled into the nostrils of non-anesthetized mice with a micropipettor (5 μl/nostril). Treated mice were infected per os with 50 cysts of 76 K Toxoplasma strain, 1 month post-treatment, and followed up by clinical examination for a further period of 6 weeks.

Study of Humoral Immune Responses

Specific Toxoplasma IgG were quantified in the sera of treated mice by ELISA. IgG synthesis against Toxoplasma antigens was monitored sequentially in sera. The results are shown in FIG. 1.

Figure 1:
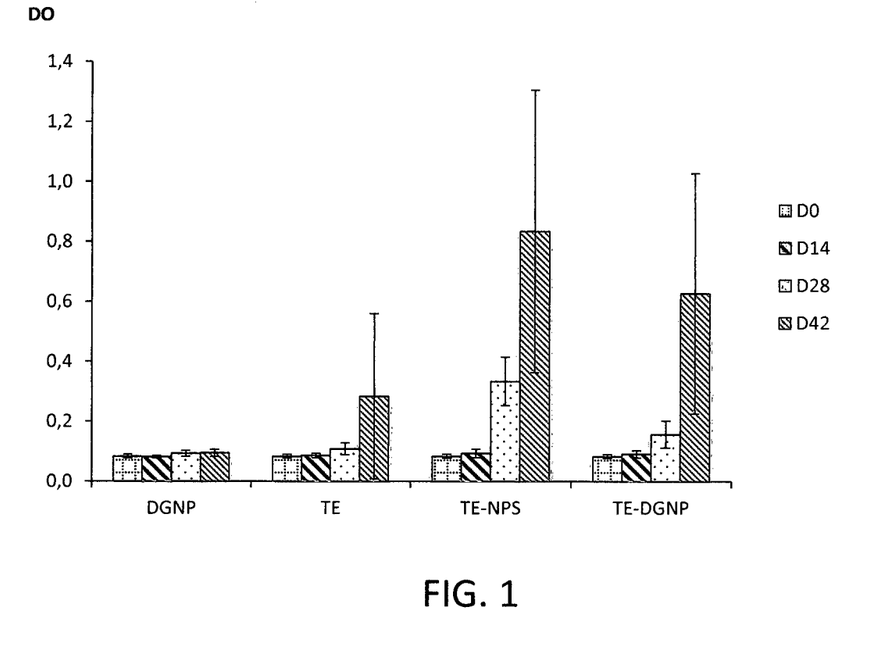
FIG. 1 shows the ELISA analysis of *T. gondii* IgG antibodies in serum of Swiss mice treated with three intranasal administrations (15-days interval between each administration) of DGNP (dipalmitoyl phosphatidyl glycerol nanoparticles), TE (total antigen extract), a mixture of TE and NPS (nanoparticles), and a mixture of TE and DGNP, for which the analyses are performed the day of the first administration, 14 days after the first administration (second administration), 28 days after the first administration (third administration), and finally 42 days after the first administration, respectively.

FIG. 1 shows the optical density (DO), measured in the sera of the treated mice. The optical density shows the level of serum IgG against T. gondii. DGNP refers to the mice treated with DGNP alone before infection, TE refers to the mice treated with the total antigen extract (TE) alone before infection, TE-NPS refers to the mice treated with the mixture of TE and NPS before infection and TE-DGNP refers to the mice treated with the mixture of TE and DGNP, before infection. DO refers to the optical density measured before treatment for each group of treated mice. D14 refers to the optical density measured 14 days after the first intranasal administration, D28 refers to the optical density measured 14 days after the second intranasal administration and D42 refers to the optical density measured 14 days after the third intranasal administration.

As shown in FIG. 1, specific Toxoplasma IgGs could be detected after the second intranasal administration in the groups of mice immunized with TE-NPS or TE-DGNP. The boost effect due to the third intranasal administration resulted in a strong induction of IgG expression, but no significant difference was observed between the two nanoparticles. No IgGs were detected in the group of mice treated with TE alone.

Study of Cellular Immune Responses:

To investigate cellular immune responses, splenocyte cytokines, a strong immunogenicity biomarker of vaccine efficacy, were analyzed in supernatants of Toxoplasma-stimulated splenocytes from the previously-mentioned treated mice, 3 weeks after the third intranasal administration. Cytokines (IFN-γ, IL-12, IL-10, IL-13, TNF-α, IL-5) were quantified by ELISA.

As T-cell-derived IFN-γ was also a valuable hallmark of protective immunity in toxoplasmosis, IFN-γ was determined by ELI spot analysis after Toxoplasma antigen stimulation.

To investigate the cellular immune response induced after treatment with TE-NPS, TE-DGNP, TE alone, or nanoparticles alone, the supernatants of cultured cells from the spleen of 2 mice from the different groups were evaluated for the production of IFN-γ, IL-10, and IL-12 in response to TE restimulation (10 μg×ml$^{-1}$).

Figure 2:
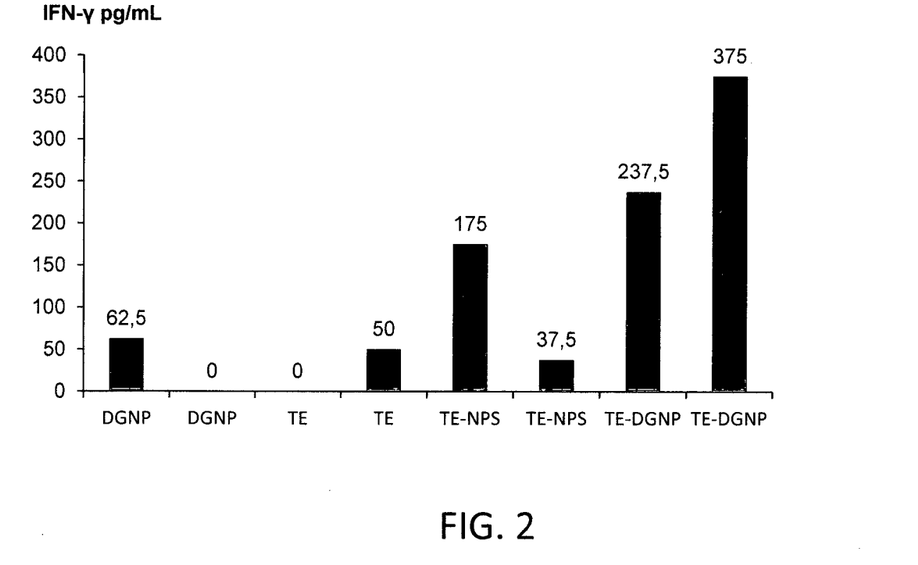
FIG. 2 shows ELISA analysis of IFN-γ in supernatants of cultured splenocytes obtained from the groups of treated mice as explained in FIG. 1, after the third intranasal administration.

FIG. 2 shows the concentration of IFN-γ (pg/mL) in supernatants of cultured splenocytes obtained from the above-mentioned groups of treated mice.

Each column referred to as DGNP corresponds to a mouse treated with DGNP alone. Each column referred to as TE corresponds to a mouse treated with TE alone. Each column referred to as TE-NPS corresponds to a mouse treated with a mixture of TE and NPS. Each column referred to as TE-DGNP corresponds to a mouse treated with a mixture of TE and DGNP.

As shown in FIG. 2, only one mouse immunized with the mixture of TE and NPS responded to TE stimulation by the production of IFN-γ by spleen cells (175 pg/ml). On the other hand, as shown in FIG. 2, a specific production of IFN-γ by spleen cells of the 2 mice immunized with the mixture of TE and DGNP was observed (237 and 375 pg/ml, respectively). Consequently, DGNP seems to be more efficient at inducing a cellular immune response.

Evaluation of the Amount of Cysts in the Brain of Mice Treated with a Mixture of TE and DGNP Six weeks after *T. gondii* infection, mice treated with a mixture of TE and DGNP and then infected with *T. gondii* were killed and their brains were collected.

Brains were harvested 6 weeks after infection from surviving mice and homogenized in 5 mL of RPMI 1640 with a pestle and mortar. The cysts in each brain homogenate were counted under a microscope (10 counts, each on 10 µl). The results are expressed as Mean±SEM for each group. The data were statistically analysed using the Mann-Whitney U test (GraphPad prism software), (p<0.05). The results are shown in FIG. 3.

Figure 3:
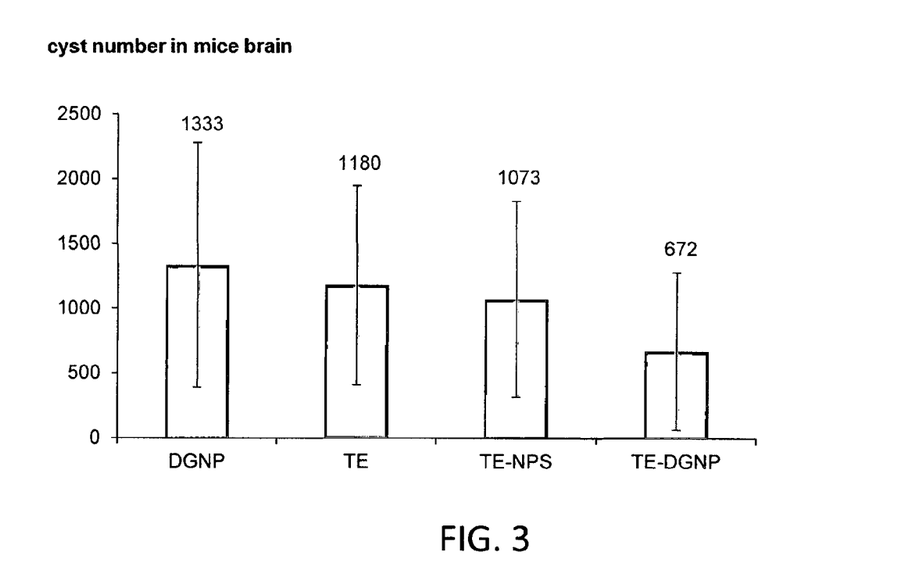
FIG. 3 shows the parasite loads of mice brains obtained by microscopic counting after brain homogenization in the groups of treated mice as referred to in FIG. 1 and after infection with *T. gondii* cysts, for which the results are obtained 6 weeks after *T. gondii* infection.

FIG. 3 shows the number of cysts in mice brain for the mice treated before infection by *T. gondii*, with DGNP alone (referred as DGNP), TE alone (referred as TE), with the mixture of TE and NPS (referred as TE-NPS), and with the mixture of TE and DGNP (referred to as TE-DGNP).

As shown in FIG. 3, mice treated with the mixture of TE and DGNP had significantly fewer cysts than mice treated with DGNP, TE, and the mixture of TE and NPS, respectively (672, 1333, 1180 and 1072, respectively; p<0.05). Mice treated with the mixture of TE and DGNP have 56% less cysts in their brains. These results suggest that treatment (vaccination) with the mixture of TE and DGNP induces a cellular immune response and then reduces the spread of parasites and the formation of cysts in the brain.

According to the obtained results, DGNP nanoparticles were used for the following experiments of vaccination and to compare the vaccination protocol with DGNP, to the vaccination protocol with cholera toxin (CT).

Comparison Between DGNP and Cholera Toxin (CT)

Six groups of 10 CBA/J mice were treated with three intranasal administrations at 15-day intervals with TE (10 µg), nanoparticles (DGNP—30 µg), Cholera Toxin (CT—0.5 µg) alone (defined as control groups), with the combination TE+DGNP, and TE+CT (10 µg of TE and 30 µg of DGNP or 0.5 µg of CT), respectively. The experimental design includes a group of untreated mice.

Each dose of the above-mentioned toxin, nanoparticles and combinations (mixtures) was diluted to a final volume of 10 µl in phosphate-buffered saline (10 mM phosphate, 140 mM NaCl [PBS]) and instilled into the nostrils of non-anesthetized mice with a micropipettor (5 µl/nostril). Five independent experiments were performed.

Figure 4:
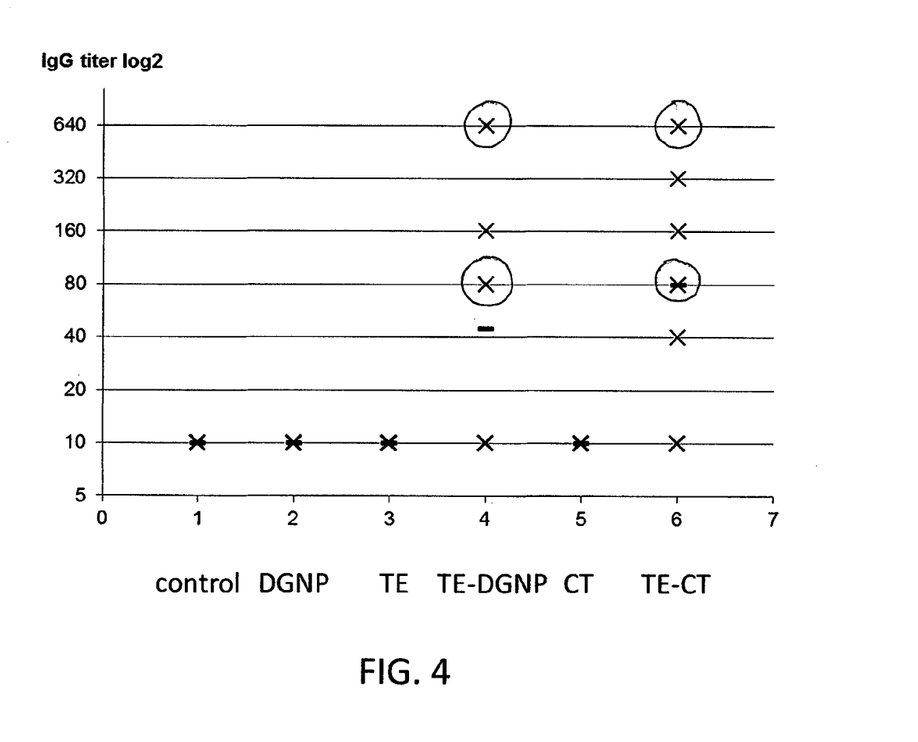
FIG. 4 shows the results of the humoral analysis of *Toxoplasma* IgG antibodies in serum of CBA/J mice treated with three intranasal administrations of TE alone, DGNP alone, a mixture of TE and DGNP, cholera toxin (CT) alone, and a mixture of TE and CT, respectively, said results being obtained 14 days after the third intranasal administration, in which the crosses refer to mice whereas the dashes refer to the average value obtained for each group of mice; the crosses referring to the mice having the stronger response in the groups treated with a mixture of TE and DGNP and with a mixture of TE and CT, respectively, are surrounded; the crosses referring to mice showing an average humoral response for each of the previously cited groups are also surrounded.

Analysis of the Humoral Response:

IgG synthesis against *Toxoplasma* antigens was monitored in sera 14 days after the third intranasal administration. The experimental protocol is described in reference to FIG. 1. The results are shown in FIG. 4. FIG. 4 shows the optical density of sera obtained from the above-mentioned treated mice. The specific antibody titer is given as the reciprocal of the highest dilution producing an optical density (OD) that was 2.5-fold greater than that of untreated mice sera at the same dilution. Results are expressed as the mean log titers and standard deviation (S.D).

As shown in FIG. 4, specific *Toxoplasma* IgGs are detected in the groups of mice treated with the mixture of TE and DGNP and the mixture of TE and CT. As shown in FIG. 4, no significant difference was observed between the two groups. No IgGs were detected in the group of mice immunized with TE, CT, or DGNP alone.

Analysis of the Cellular Response:

To investigate the cellular immune response induced after treatment as above-described, the supernatants of cultured cells from the spleens of 2 mice from the hereinbefore identified groups were evaluated for the production of IFN-γ, IL-10, IL-13, TNF-α, IL-5, and IL-12 in response to TE restimulation with an ELISA analysis and IFN-γ with an Elispot. The results are shown in FIG. 5.

Figure 5:
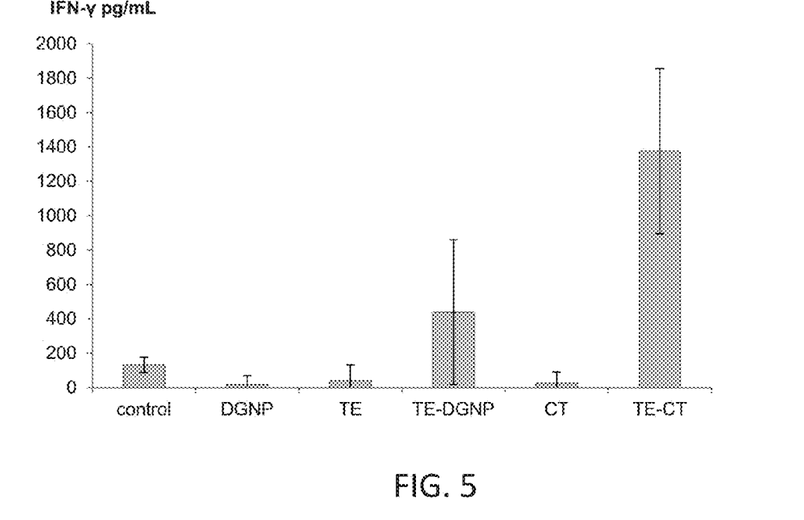
FIG. 5 shows the ELISA analysis of IFN-γ (pg/ml) in supernatants of cultured splenocytes for each group as referred to in FIG. 4 and after the third intranasal administration.

FIG. 5 shows the concentration of IFN-γ (pg/mL) in supernatants of cultured splenocytes for two mice of each group as previously defined.

As shown in FIG. 5, both mice immunized with the mixture of TE and DGNP; and mice treated with the mixture of TE and TC, responded to TE stimulation by the production of IFN-γ by spleen cells. Mice immunized with a mixture of TE and DGNP produce more than 400 pg/mL of IFN-γ. Mice treated with TE and CT produce around 1400 pg/mL of IFN-γ.

The IFN-γ production by splenocytes was also measured two weeks after the third intra-nasal administration. The results are shown in FIG. 6.

Figure 6:
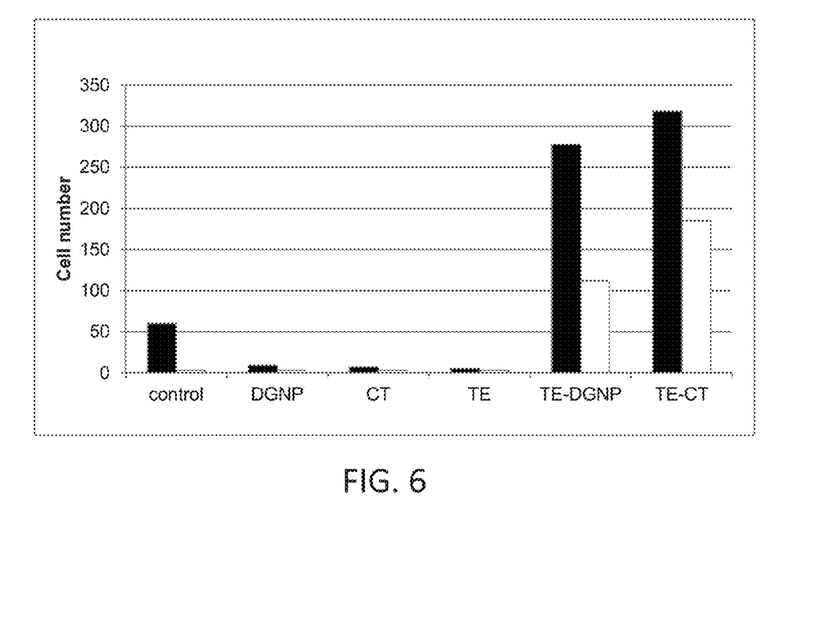
FIG. 6 shows the production of IFN-γ by splenocytes produced in each group of mice as defined in reference to FIG. 4, two weeks after the third intranasal administration; the black columns refer to the IFN-γ production of the mice having the stronger humoral response, in the TE-DGNP and in the TE-CT group, respectively, whereas the white columns refer to the IFN-γ production of the mice having an average humoral response, in the TE-DGNP and in the TE-CT group, respectively.

FIG. 6 shows the IFN-γ production for two mice of each group shown in FIG. 4. As regards the group treated with a mixture of DGNP and TE (DGNP-TE), and the group treated with a mixture of TE and CT (TE-CT), the results are obtained for the mice referred to by surrounded crosses. As shown in FIG. 6, the production of IFN-γ by splenocytes is increased in the mice vaccinated with a mixture of DGNP and TE. IL-12, IL-13, TNF-α, and IL-5 release was not detected in any of the samples analyzed.

Test of Infection

Mice treated with three intranasal administrations of DGNP alone, TE alone, the mixture of TE and DGNP, CT alone, and the mixture of CT and DGNP, respectively, were orally infected with cysts of the 76K strain of *T. gondii*. A group of non-treated mice was also infected as a control.

Percentage of Survival

The survival of each group was followed up during 30 days after the infection with 80 cysts. The total number of tested animals in each group is n=8.

Except one mouse in the group control, all mice rapidly show clinical symptoms of disease, lost body weight and were dead within 11 days after infection, while 100% of the mice vaccinated with the mixture of TE and DGNP survived over the experimental period of 30 days.

Number of Cysts in Mice Brain

Mice of each treated group were orally infected with 50 cysts and sacrificed one month after the oral infection. Protection against *T. gondii* was evaluated by measuring mouse brain cyst number (three experiments with 50 cysts). The total number of tested animals in each group is n=8. The protocol is as described in reference of FIG. 3. The results are shown in FIG. 7.

Figure 7:
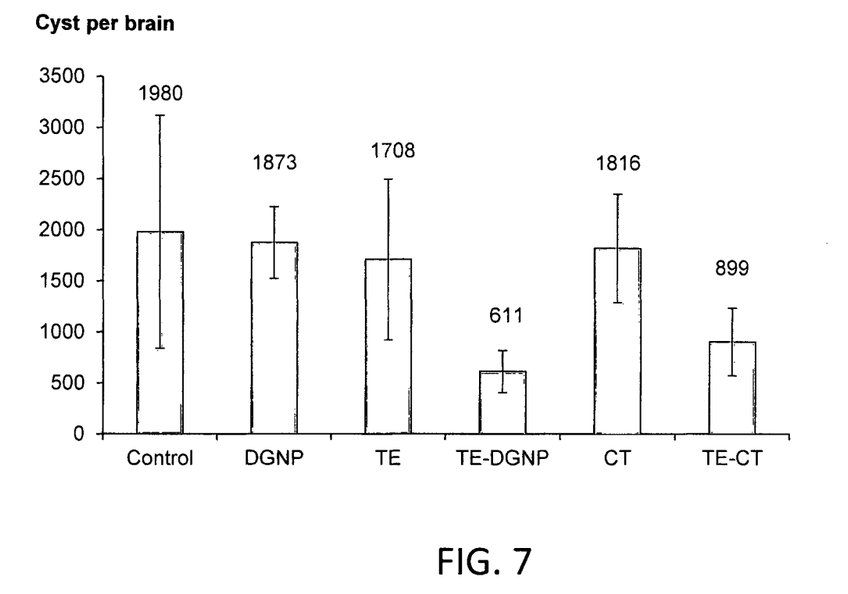
FIG. 7 shows the number of cysts in mice brain for the group of mice untreated, mice treated with three intranasal administrations of DGNP alone, mice treated with three intranasal administrations of TE alone, mice treated with three intranasal administrations of a mixture of TE and DGNP, mice treated with three intranasal administrations of CT alone, and mice treated with three intranasal administrations of a mixture of TE and CT, respectively, said number of cysts being obtained two weeks after the third intranasal administration.

FIG. 7 shows the number of cysts in the mice brains of each group. As shown in FIG. 8, mice treated with the mixture of TE and DGNP before infection with *T. gondii*, have significantly fewer cysts than control mice (611 versus 1980 cysts, respectively; p<0.01), which represents a 70% reduction. The group of mice treated with a mixture of TE and DGPN has fewer cysts than the group treated with the mixture of TE and CT. The above-mentioned results suggest that vaccination with the mixture of DGNP and TE provides a long term protection.

What is claimed is:

1. A pharmaceutical composition comprising, as an active ingredient, a mixture of:
    a solid nanoparticle comprising a porous cationic-polysaccharide core loaded with at least an anionic phospholipid and without any phospholipidic layer surrounding said porous cationic-polysaccharide core;
    at least an antigen obtained from an intracellular pathogenic agent; and
    a pharmaceutically acceptable solvent.

2. The pharmaceutical composition according to claim 1, wherein said porous cationic polysaccharide core comprises a crosslinked polymer obtained by a reaction between:
    a polysaccharide selected from the group consisting of a starch, a dextran, a dextrin, and a maltodextrin, and
    at least one cationic ligand selected from the group consisting of a primary amine, a secondary amine, a tertiary amine and a quaternary ammonium.

3. The pharmaceutical composition according to claim 1, wherein said anionic phospholipid is comprises glycerol phospholipid.

4. The pharmaceutical composition according to claim 1, wherein said intracellular pathogenic agent is selected from the group consisting of a virus, a bacteria, a mycobacteria, and a fungus.

5. The pharmaceutical composition according to claim 1, wherein said intracellular pathogenic agent is an intracellular parasite.

6. The pharmaceutical composition according to claim 1, wherein said antigen is obtained from a previously killed pathogenic agent.

7. The pharmaceutical composition according to claim 6, wherein said antigen is obtained from a tachyzoite form of said previously killed pathogenic agent.

8. A vaccine against an intracellular pathogen comprising the pharmaceutical composition according to claim 1 and further comprising a pharmaceutically acceptable additive selected from the group consisting of a suitable excipient, a suitable carrier, and a suitable vehicle.

9. A vaccine adjuvant comprising a solid nanoparticle comprising a porous cationic-polysaccharide core loaded with at least an anionic phospholipid and without any phospholipidic layer surrounding said core.

10. A method for eliciting an immune response against an intracellular pathogen in a patient in need of such treatment, said method comprising administrating to said patient a therapeutic amount of a composition according to claim 1.

11. The method according to claim 10, wherein said composition is intranasally administered.

12. The method according to claim 10, wherein said administering to said patient the therapeutic amount of the composition according to claim 1 is effective to cause a Th1 type immune response in said patient.

13. The method according to claim 10, wherein said patient is in need of a prophylactic treatment against said intracellular pathogenic agent.

14. The method according to claim 10, wherein said patient is selected from the group consisting of a human, a non-human primate, an ovine, a canine, a feline, a murine, a bovine, an equine, a porcine, and a bird.

15. The pharmaceutical composition according to claim 3, wherein said anionic phospholipid is a diacylphosphatidyl glycerol.

16. The pharmaceutical composition according to claim 15, wherein said diacylphosphatidyl glycerol is selected from the group consisting of dipalmitoylphosphatidylglycerol, diacylphosphatidyl serine and diacylphosphatidylinositol.

17. The pharmaceutical composition according to claim 4, wherein said intracellular pathogenic agent is selected from the group consisting of herpes simplex virus 1, herpes simplex virus 2, Human papilloma virus, Epstein-Barr virus, cytomegalovirus, *Mycobacterium tuberculosis*, dengue fever virus, human immunodeficiency virus, Human respiratory syncytial virus (RSV), hepatitis A virus, hepatitis B virus, and hepatitis C virus.

18. The pharmaceutical composition according to claim 5, wherein said intracellular pathogenic agent is selected from the group consisting of *Toxoplasma gondii, Emeria* spp., *Neospora caninum, Sarcocystis* spp., *Plasmodium* spp., *Cryptosporidium* spp., *Acanthamoeba* spp., *Babesia* spp., *Balantidium coli, Blastocystis, Dientamoeba fragilis, Entamoeba histolytica, Giardia lamblia, Isospora belli, Leishmania* spp., *Naegleria fowleri, Rhinosporidium seeberi, Trichomonas vaginalis, Trypanosoma brucei,* and *Trypanosoma cruzi*.

19. The pharmaceutical composition according to claim 1, comprising a dose having between 5 μg and 1 mg of the at least an antigen.

20. The pharmaceutical composition according to claim 1, wherein the solid nanoparticle is 60 nm.

* * * * *